United States Patent
D'Amelio, Sr.

(10) Patent No.: US 8,551,540 B1
(45) Date of Patent: *Oct. 8, 2013

(54) STABILIZING AND ANTIOXIDANT COMPOSITION CONTAINING SAW PALMETTO BERRY COMPONENT AND METHOD OF USE

(75) Inventor: Frank S. D'Amelio, Sr., Cold Spring Harbor, NY (US)

(73) Assignee: Bio-Botanica, Inc., Happauge, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/558,399

(22) Filed: Jul. 26, 2012

Related U.S. Application Data

(60) Division of application No. 11/606,352, filed on Nov. 30, 2006, now Pat. No. 8,252,347, which is a continuation-in-part of application No. 10/785,478, filed on Feb. 25, 2004, now abandoned.

(60) Provisional application No. 60/449,438, filed on Feb. 25, 2003.

(51) Int. Cl.
*A61K 36/889* (2006.01)

(52) U.S. Cl.
USPC ......................................................... 424/727

(58) Field of Classification Search
None
See application file for complete search history.

(56) References Cited

U.S. PATENT DOCUMENTS

| | | | |
|---|---|---|---|
| 5,972,345 | A | 10/1999 | Chizick et al. |
| 6,039,950 | A | 3/2000 | Khwaja et al. |
| 6,132,727 | A | 10/2000 | Rohde et al. |
| 6,241,987 | B1 | 6/2001 | Lam |
| 6,261,607 | B1 | 7/2001 | Newmark et al. |
| 6,277,417 | B1 | 8/2001 | Anderson |
| 6,319,524 | B1 * | 11/2001 | Gregg, Jr. ............ 424/727 |
| 6,358,541 | B1 * | 3/2002 | Goodman ............ 424/727 |
| 6,544,581 | B1 | 4/2003 | Shrikhande et al. |
| 6,998,501 | B1 | 2/2006 | Wright et al. |
| 2001/0028897 | A1 * | 10/2001 | Hammerly ............ 424/727 |

OTHER PUBLICATIONS

Tong et al., Journal of American Oil Chemists' Society, Aug. 29, 2002, vol. 79, No. 12, pp. 1201-1206, Abstract only.

* cited by examiner

*Primary Examiner* — Christopher R Tate
*Assistant Examiner* — Deborah Davis
(74) *Attorney, Agent, or Firm* — Roylance, Abrams, Berdo & Goodman, L.L.P.

(57) ABSTRACT

A stabilizing and antioxidant composition is prepared from the residue obtained from the saw palmetto berry. The residue from the saw palmetto berry exhibits antioxidant properties that can be used to stabilize various compositions such as food or edible compositions and cosmetics. The saw palmetto residue is also delivered topically or orally to a patient to administer an effective amount of an antioxidant to a patient.

17 Claims, No Drawings

US 8,551,540 B1

STABILIZING AND ANTIOXIDANT COMPOSITION CONTAINING SAW PALMETTO BERRY COMPONENT AND METHOD OF USE

CROSS-REFERENCE TO RELATED APPLICATIONS

This application is a divisional application of Ser. No. 11/606,352, filed Nov. 30, 2006 now U.S. Pat. No. 8,252,347, which is a continuation-in-part of application Ser. No. 10/785,478, now abandoned which application claims the benefit under 35 U.S.C. §119(e) of prior provisional application No. 60/449,438, filed Feb. 25, 2003, which are hereby incorporated by reference in their entirety.

FIELD OF THE INVENTION

The present invention is directed to a stabilizing composition containing a fraction obtained from saw palmetto berries. The invention is also directed to a process of administering an antioxidant where the antioxidant is obtained from the residue after an oil extraction process from saw palmetto berries.

BACKGROUND OF THE INVENTION

Saw palmetto (Serenoa repens) is a small, shrub-like palm that grows in the southeastern United States. The saw palmetto produces leaves with one-ribbed segments and a seed stalk in late spring. The stalk produces flowers which develop a hard green fruit about the size of an olive with one seed. The fruit ripens in the summer and turns various shades of yellow, orange and black. The fruit is harvested in late summer, and typically yields several hundred pounds of berries per acre.

Saw palmetto berries have been consumed and used by Native Americans for many centuries for various purposes. In recent times, a tea made from saw palmetto berries has been used as a mild diuretic and for genitourinary treatments. Various herbs and plant materials have been commonly used in various parts of the world for centuries for medicinal uses. In recent years in the United States, plant materials including saw palmetto berries have shown increased use to treat various illnesses. The plant or botanical materials are typically used in the form of powders or extracts made from one or more plants. The extracts can be obtained from the whole plant or from selected parts such as the leaves, seeds or roots. The resulting powder and extracts are a complex mixture of various compounds and can contain many biologically active and biologically inactive compounds.

The complex nature of plant materials and plant extracts make it difficult to identify the active components and isolate the active an inactive compounds. The complex nature of the extracts also makes it difficult to control the amount or ratio of the various components and the concentration of the compounds within the extracts. The variations in chemical composition from different batches of plant materials obtained from different harvests results in inconsistent treatments. However, the complex nature of the various bioactive components in botanical materials provide the potential for identifying and utilizing various synergistic bioactive profiles.

A great deal of effort has been spent on identifying the various components in the plant materials, and particularly the extracts. The ability to isolate and identify the components has increased with the development of improved chemical separation and analytical technology. The isolation and purification of various compounds from plant materials has been a common form of drug research. There has also been an increased interest in studying the complex medicinal and biological activities. Many plant extracts have potent activities, but the variations in the compositions result in unpredictable and inconsistent properties.

The saw palmetto berry has been used for a variety of purposes. The saw palmetto berry has been used to make a tea or infusion, dried and ground to a powder or to obtain an oil extract. One common use is the treatment of benign prostatic hypertrophy. The saw palmetto berry extract has been shown to be nontoxic and has demonstrated few or no adverse side effects. One example of a process for obtaining and determining the bioactivity of the extract of the saw palmetto berry is disclosed in U.S. Pat. No. 6,039,950 to Khwaja et al.

U.S. Pat. No. 6,197,309 to Wheeler discloses a composition for treating prostate disorders. The composition includes a mixture of various vitamins, amino acids and plant materials. The plant materials include a mixture of saw palmetto berries, pumpkin seeds, stinging nettle, garlic and Ginkgo leaves.

U.S. Pat. No. 6,241,987 to Lam discloses a dietary supplement for supporting and maintaining prostate gland function. The composition contains a mixture of saw palmetto oil extracts, pumpkin seed extract and nettle root extract. The combination of the extracts are purported to provide a synergistic effect.

Plant extracts are obtained by various processes depending on the desired composition of the resulting extract. Typically, the extracts are obtained from the dried plant material by liquid extraction. The liquid extraction can use water, alcohol or various other organic solvents. One common extraction process uses liquid or supercritical carbon dioxide. An example of a carbon dioxide extraction process of saw palmetto berries is disclosed in U.S. Pat. No. 6,319,524 to Gregg.

SUMMARY OF THE INVENTION

The present invention is directed to a composition containing the residue from saw palmetto berries. The invention is also directed to a process for stabilizing a composition using saw palmetto berry fraction.

Accordingly, a primary aspect of the invention is directed to the discovery that the saw palmetto berry, and particularly, the oil from saw palmetto berries, can provide a stabilizing effect to various compositions and that the saw palmetto berry and the oil contains compounds that have antioxidant properties.

Another aspect of the invention is to provide a stabilizing composition containing the residue from saw palmetto berries that remains after an oil extraction process. In a further embodiment, the invention provides a stabilizing composition containing the residue from was palmetto oil obtained from an oil extraction process.

A further aspect of the invention is to provide an antioxidant composition containing a selected solid fraction from saw palmetto berry oil without the oil fraction and without the pomace or marc. The pomace or marc fraction is substantially insoluble in aqueous and organic solvents.

Still another aspect of the invention is to provide an antioxidant composition containing a substantially lipid-free component or fraction from saw palmetto berries. The lipid-free component is the residue that remains after the lipids, including the fats and oils and other hydrophobic extractable compounds and materials, are removed from the whole dried saw palmetto berries.

Another aspect of the invention is to provide an antioxidant composition containing the solid residue recovered from oil fraction obtained from an oil extraction process from saw palmetto berries. Typically, the oil extraction process is a non-aqueous extraction that extracts a substantial portion of the lipids and soluble hydrophobic components in addition to other extractable components. In one embodiment, the oil fraction is recovered and evaporated to concentrate the oil and remove all or substantially all of the organic extraction solvents. The resulting oil separates into an oil fraction and a solid precipitate residue. The residue is recovered to obtain a solid that is substantially free of soluble and extractable sterols and fatty acids.

A further aspect of the invention is to provide a stabilizing composition containing a fraction from saw palmetto berries as the primary stabilizing agent. The composition containing the saw palmetto fraction is suitable for use in stabilizing various oils, food products, cosmetics and other compounds that can degrade by auto-oxidation or free radical degradation.

Another aspect of the invention is to provide a process for stabilizing a composition by the addition of an effective amount of a stabilizing agent. The stabilizing agent contains a fraction of saw palmetto berries having stabilizing and particularly antioxidant properties.

Still another aspect of the invention is to provide a dietary supplement containing a prescribed unit dosage of an antioxidant. The antioxidant is obtained from a fraction of saw palmetto berries. In one embodiment, the residue remaining after an oil extraction process from saw palmetto berries is used as the source of the antioxidant.

A further aspect of the invention is to provide a topical composition containing an antioxidant obtained from saw palmetto berries. A residue obtained from an oil extraction process from saw palmetto berries is used as a source of the antioxidant.

Another aspect of the invention is to provide a process for administering internally to a patient an effective amount of an antioxidant where the antioxidant is obtained from saw palmetto berries.

The various aspects of the invention are basically attained by providing a process for stabilizing a composition. The process comprises the step of admixing or contacting a stabilizing agent with the composition in an amount effective to stabilize the composition. The stabilizing agent is a residue obtained from an oil extraction process from saw palmetto berries.

The aspects of the invention are also obtained by providing a stabilizing composition comprising a stabilizing agent in an amount effective to stabilize a composition. The stabilizing agent comprises a residue obtained from an oil extraction process from saw palmetto berries.

The aspects of the invention are further obtained by providing a dietary supplement composition for orally administering to a mammal. The dietary supplement comprises a source of an antioxidant. The source of an antioxidant comprises a residue obtained from an oil extraction process from saw palmetto berries. The residue is included in an amount effective to provide an effective dosage of the antioxidant to the mammal.

The aspects of the invention are also attained by providing a topical composition for applying topically to a mammal. The composition comprises a vehicle and a source of an antioxidant. The source of the antioxidant is a residue obtained from an oil extraction process from saw palmetto berries and is included in an amount effective to treat the skin of a subject with the antioxidant.

These and other aspects of the invention will become apparent in the following detailed description of the invention which disclose various embodiments of the invention.

DETAILED DESCRIPTION OF THE INVENTION

The present invention is directed to a stabilizing agent and to a process for stabilizing a composition. The invention is also directed to a composition and to a process for administering an antioxidant to a subject either topically or internally.

The invention is particularly directed to the discovery that the fruit and seed from the saw palmetto contain compounds that exhibit stabilizing properties to various compositions. In addition, it has been discovered that a certain fraction from the saw palmetto exhibits stabilizing and antioxidant properties and can be used as a source of an antioxidant to stabilize compositions and to deliver a unit dosage of an antioxidant to humans and other animals. Although not completely understood, the antioxidant composition of the invention is believed to have oxygen scavenging properties that is effective in inhibiting oxidation of the composition.

The saw palmetto plant referred to herein is the species *Serenoa repens* that grows in the southeastern United States. The saw palmetto berry referred to herein is the black ripened fruit and seed. The saw palmetto berry of the invention can be used soon after harvesting or in a dried form. Typically, the saw palmetto berry is dried for extended storage before processing to obtain the composition of the invention.

The methods and compositions of the invention in one preferred embodiment use a fraction of the saw palmetto berry that has been found to have antioxidant properties and stabilizing properties when used in effective amounts in various products such as foods and cosmetics. One process of the invention contacts a composition with a stabilizing agent in an amount effective to stabilize the composition where the stabilizing agent is a fraction from saw palmetto berries. In particular, the invention is directed to methods and compositions that utilize the antioxidant properties of the residue from the saw palmetto berry and a precipitate obtained from the saw palmetto oil after solvent extraction and separation of the pomace or marc. In one embodiment, the residue or precipitate from the saw palmetto berry is contacted with the composition to stabilize the composition using an amount of about 5 wt % or less and preferably about 1.0 wt %, based on the total weight of the composition.

A fraction from saw palmetto berries is an effective stabilizing agent and antioxidant agent for stabilizing various compositions. The fraction is also effective for internal human consumption as an antioxidant source. In preferred embodiments, the fraction is a saw palmetto residue. The saw palmetto residue in one embodiment refers to the residual material that remains after the saw palmetto berries have been subjected to an extraction process and particularly after subjecting to an oil extraction process. In one embodiment, the residue or residual material of the prior extraction processes is typically considered a waste product and that is discarded after the oils and other extractable compounds are extracted. The residue is an insoluble solid that has all or substantially all of the soluble compounds extracted from the berries. The saw palmetto residue, in addition to the pulp and fibrous portions, contains residual compounds that are either insoluble in aqueous or organic solvents or that cannot be extracted by conventional extraction processes. It is believed that the insoluble compounds in the residue have antioxidant and stabilizing properties. In another preferred embodiment, the residue refers to the solid material that precipitates and is recovered from the oil fraction which is extracted from the saw palmetto berry. The solid precipitate in this embodiment may retain small amounts of oil or water soluble compounds that are entrapped and cannot be extracted using standard extraction processes. In one embodiment, the solid precipitate is substantially oil free and is free of the pomace and the marc.

The saw palmetto residue of the invention is obtained from a suitable extraction process that is intended to recover the various lipid soluble and hydrophobic components from the whole saw palmetto fruit. The extraction process typically produces an extract containing sterols, commonly referred to as phytosterols, and various lipids, including triglycerides, fatty acids and fatty acid esters. In preferred embodiments of the invention, the residue from the oil extraction from the saw palmetto berries has substantially all of the extractable compounds removed from the residue. The residue of the saw palmetto berries is referred to as being substantially "lipid-free" when all or substantially all of the extractable lipids and hydrophobic compounds are removed. The lipids include the extractable fats and oils. The extract obtained by the extraction process contains fatty acids, fatty acid esters, tannins, colorants, invert sugars, mannitol and the phytosterols, β-sitosterol, campesterol, stigmasterol and cycloartenol. The lipid fraction generally contains long chain fatty acids and aliphatic hydrocarbons, fatty alcohols, amines, amino alcohols, aldehydes, triglycerides, waxes, phytosterols, phospholipids, glycolipids and sphingolipids. The fatty acid esters are typically the ethyl esters and triglycerides.

Common extraction processes that can be used to extract the oil phase and to produce the residue of the invention include supercritical carbon dioxide, lower alcohols, acetone, and hexane. In a preferred embodiment, the extraction solvent is selected from the group consisting of methanol, ethanol, and hexane, and mixtures thereof. The extraction medium can be an aqueous mixture of one or more miscible organic solvents. Typically, the alcohol that is used to obtain an extract for human consumption is ethanol. Methanol can also be used where the toxicity of any residual methanol is not a concern. In a preferred embodiment, the oil extraction method from the dried saw palmetto berries uses an alcohol or other polar organic solvent. Polar solvents and particularly lower alcohols have been found to extract substantial amounts of the antioxidant compounds from the plant material which is recovered in the oil fraction. As discussed below, the antioxidant compounds are precipitated and recovered from the oil fraction in one embodiment of the invention. In other embodiments, the residue is obtained from a steam extraction process.

The extraction process to obtain the residue of the invention utilizes solvent extraction steps as known in the art. The extraction process usually comprises drying the saw palmetto berries to reduce the moisture content to about 3 wt % or less. The ripe saw palmetto berries generally contains about 66 wt % water and will spoil in a short period of time. Generally, saw palmetto berries are harvested and dried at 130° to 140° F. for several days to produce dried berries that are stable for an extended period of time. The dried berries are packaged and stored for extended periods without deterioration. The dried berries are available commercially and are readily amenable to conventional extraction processes.

Prior to the solvent extraction, the dried saw palmetto berries are reduced in size typically by grinding to a particle size that is amenable to the solvent extraction. In one embodiment, the saw palmetto berries are ground to a particle size of about 60 mesh or less. The ground powder of the saw palmetto berries is extracted in a suitable extraction vessel where the extraction solvent is passed through the powder. Sequential separations can be obtained where each separation usually contains different compounds and different ratios of compounds. The different extractions can be used separately or combined to form a holistic mixture. The solutions are evaporated to obtain the oily, lipid phase. Typically, the solvent vapors are recovered and recycled to the extraction process.

In an alternative embodiment, the extraction solvent is a substantially non-polar solvent that is liquid at room temperature. An example of a non-polar solvent that can be used to extract the oils and hydrophobic compounds is hexane. The non-polar solvent has a low boiling point that can easily be evaporated and separated from the oils and to recover the residue without the need for further processing of the residue. Non-polar solvents are generally preferred when the antioxidant components are to remain in the pomace or marc since non-polar solvents generally remove only the oil fraction and do not remove large amounts of the antioxidant components. Polar solvents are preferred when the antioxidants are to be extracted with the oil.

In one preferred embodiment, the saw palmetto plant material is placed in a percolator or other vessel and a menstruum or other extraction solvent is passed through the plant material. The extraction using the menstruum is continued to exhaust the plant material from all or substantially all of the active constituents and oil. Preferably, the percolation continues until no oil remains in the plant material.

The menstruum or extraction solvent is recovered and placed in a suitable vessel to remove the solvent. The solvents can be removed under vacuum or reduced pressure and by heating. Preferably, the extraction solvents are sufficiently volatile to be removed from the saw palmetto oil by gentle heating and/or vacuum. As the oil and the solvent mixture are evaporated and oil is concentrated, the saw palmetto oil separates into two immiscible materials. The oil fraction forms a top layer and solid fraction precipitates from the oil as an oil insoluble material. The solid fraction is recovered from the oil by filtration, centrifuging or decanting. The oil insoluble fraction or solid is referred to as a precipitate.

The resulting solid fraction residue or filtrate that is separated from the oil extract from the saw palmetto plant material have antioxidant properties. In one preferred embodiment, the antioxidant composition is a residue or filtrate obtained from the oil fraction after the oil is clarified. The antioxidant composition in this embodiment is substantially free of the fibrous pomace, marc, other solid plant materials, and substantially free of the saw palmetto oil.

In one embodiment, the saw palmetto plant material is extracted with an alcohol or aqueous alcohol mixture to extract all or substantially all of the extractable components and the oil. The resulting extract is heated to remove the alcohol and to concentrate the oil. As the alcohol is removed and the oil fraction is concentrated, the oil insoluble material precipitates which is recovered form the oil as an antioxidant composition. The resulting antioxidant in one embodiment is substantially oil free.

In preferred embodiments, the extraction solvent is a lower alcohol such as methanol, ethanol, or mixtures thereof. The extraction solvent can be pure alcohol. In other embodiments, the extraction solvent is an aqueous alcohol mixture containing about 70% alcohol, preferably about 80% alcohol, and more preferably 90% alcohol where the percentages are by volume.

In an alternative embodiment, the extraction process is a supercritical carbon dioxide extraction. The extraction is carried out in an extraction vessel by contacting the ground or macerated saw palmetto berries with a supercritical, liquid phase carbon dioxide at an extraction pressure of at least about 500 bar and generally about 1550 bar. The liquid carbon dioxide is delivered from a high pressure source into the extraction vessel and directed in a manner to flow through saw palmetto powder and to contact the powder particles for sufficient time to extract the extractable compounds. The extraction is preferably carried out at a temperature of about 45° C. to about 80° C. In preferred embodiments, the liquid carbon dioxide is supplied as a continuous flow through the powder.

The liquid supercritical carbon dioxide is discharged from the extraction vessel after a sufficient time to extract the desired components. The carbon dioxide and the extract are transferred to a separation vessel where the pressure is reduced to a pressure sufficient to separate the extract from the carbon dioxide. The resulting residue of the saw palmetto berries having the extractable components removed is discharged from the extraction vessel and recovered for use in the present invention.

In another suitable extraction process using liquefied carbon dioxide, the fluid and the saw palmetto powder are supplied to an extraction vessel. The liquefied carbon dioxide can contain a carrier liquid such as water. The carried liquid is included in amounts to contain extracted components that are marginally soluble in the carbon dioxide extraction solvent. The carrier liquid is generally immiscible in the carbon dioxide extraction solvent. The result is a two-phase extraction liquid. The fluid feed containing the saw palmetto powder and the carbon dioxide extraction solvent contact each other in the extraction vessel for sufficient time to extract the various compounds into the extraction solvent. The extraction vessel typically operates at a pressure of about 450 bar to about 1200 bar and a temperature of about 50° C. to 300° C. The extract from the saw palmetto berries can be separated from the carbon dioxide extraction solvent in a phase separation device such as a decanter, a coalescer, cyclone or second extraction column. An example of this type of carbon dioxide extraction process is disclosed in U.S. Pat. No. 6,261,607, which is hereby incorporated by reference in its entirety.

Another supercritical carbon dioxide extraction process grinds the dried saw palmetto berries and extracts the extractable compounds with supercritical fluid carbon dioxide at a pressure of 400 bar to 600 bar and a temperature of about 80° C. to 120° C. The carbon dioxide fluid is removed from the extraction vessel and transferred to a separation vessel. The pressure in the separation vessel is maintained at about 280 bar to about 380 bar and a temperature of about 80° C. to about 100° C. to separate the extracted oily fraction from the extraction liquid. The pressure and temperature can be reduced through sequential steps to separate selected fractions of the extract from the extraction solvent. An example of this type of extraction process is disclosed in U.S. Pat. No. 5,120,558, which is hereby incorporated by reference in its entirety.

The residue from the oil extraction process has a substantial portion of the lipids and hydrophobic compounds removed. Typically, about 90 wt % of the lipids and extractable hydrophobic compounds are removed from the original plant material so that the plant material has about 10 wt % or less of the lipids and hydrophobic extractable compounds. Preferably, the plant material has less than 2 wt %, and more preferably less than 1 wt % of the extractable components remaining.

The resulting residue from the extraction process can be used alone as a stabilizing and/or antioxidant agent or in combination with other compounds. The residue of the saw palmetto berries can be used without further processing or treatment. In one embodiment, the residue is deodorized prior to use.

The deodorizing step can use any standard deodorizing process as known in the art. For example, the particulate residue is contacted with an adsorbent in a suitable contact vessel. Suitable adsorbents include activated charcoal, alumina, molecular sieves, diatomaceous earth and chitosan.

The residue has been found to have antioxidant properties and can be used as a stabilizing agent to stabilize various compositions. In one embodiment, the residue is used to produce a stabilizing composition comprising a carrier and the saw palmetto berry residue as a stabilizing agent. The stabilizing agent is included in an effective amount to stabilize the intended material or composition. Typically, the stabilizing composition contains at least 1 wt %, and typically at least 5 wt % of the stabilizing agent. In other embodiments, the stabilizing agent consists essentially of the saw palmetto berry residue. When saw palmetto berry fraction or residue is used as a stabilizing agent, it can be combined with a solid, liquid, gel or paste as a carrier.

A particularly suitable method of using the residue is for stabilizing a composition such as oils and lipidic compounds and compositions obtained from plant materials that can degrade or become rancid upon prolonged storage. In one embodiment, the saw palmetto residue is used as a stabilizing agent and is combined with a food product in an amount effective to provide a stabilizing effect. The amount of the residue combined with the food product can depend on the nature of the food product, the amount of the unstable components in the food product and the desired shelf life. In one embodiment of the invention, the food product is an edible plant oil or product containing edible oils. The residue is typically admixed with the food product in an amount of about 0.1 wt % to about 5 wt %, and generally about 1 wt % to about 3 wt % based on the weight of the food product. Suitable and effective amounts of the residue can be determined by one skilled in the art to attain the desired stability.

The method of the invention obtains the saw palmetto residue by extracting the oils and other extractable components from the ground dried whole berries. In one preferred embodiment, the extraction process is a supercritical carbon dioxide extraction process. The resulting residue is granulated to a particle size suitable for contacting or dispersing in a food product. In one embodiment, the residue is deodorized and used as a stabilizing agent or antioxidant agent without further processing. The granulated residue is combined directly with the food product and uniformly dispersed in the food product. In other embodiments, a suspending agent or a dispersing agent is combined with the granulated residue before admixing with the food product to disperse the saw palmetto berry residue in the food product. Suitable suspending agents and dispersing agents are conventional agents as known in the food industry. Examples of food products that can be stabilized with the saw palmetto residue include products that contain large amounts of plant oils, such as peanut butter, prepared salad dressings, and other food products containing vegetable oils. Other food products that can be stabilized using the saw palmetto residue include fruit juices and baked goods such as cookies, cakes and other confectioneries. Essentially, any food product or beverage that is susceptible to autooxidation degradation can be stabilized by the antioxidant composition.

In preferred embodiments of the invention, the composition contains an effective amount of the residue from the saw palmetto berry after the extraction process. Through various tests, observations and analysis, it has been discovered that various compounds that are retained in the residue after the extraction process exhibit antioxidant properties and are effective in stabilizing various compositions, and particularly fats and oils. In particular, it was found that a plant oil extracted from a plant seed containing the saw palmetto residue is stable for at least six months. The oil has also been found to be stable for one year when stored in contact with the saw palmetto residue without any change in color, odor or taste.

The invention is primarily directed to the discovery of the antioxidant properties of the residue from the saw palmetto berry after the extraction process. The examples of the compositions and methods of the invention refer to the use of saw palmetto residue. In other embodiments, the dried whole fruit and seeds of the saw palmetto berries can be used as the source of the antioxidant. Thus, in one embodiment, a method of stabilizing a composition admixes the whole saw palmetto berry with the composition where the berry is dried and ground to a powder having a suitable particle size. Similarly, an antioxidant can be administered to a patient as an oral composition as a source of an antioxidant where the oral composition contains the dried and ground whole saw palmetto fruit and seed.

The saw palmetto residue of the invention provides an antioxidant effect and can be taken internally as a dietary supplement or can be used topically. As used herein, the term "antioxidant" refers to the ability of the residue to scavenge oxygen, and particularly oxygen radicals, to retard the oxidation of compounds such as lipids, lipoproteins, proteins or DNA. Generally, the saw palmetto residue is used as the sole or primary antioxidant in the stabilizing composition. In one preferred embodiment, the stabilizing composition, dietary supplement and topical composition contain an antioxidant agent where the antioxidant agent and source of the antioxidant agent consists essentially of the saw palmetto residue after the oils and other extractable compounds are removed. In alternative embodiments, a secondary antioxidant can be included to supplement or enhance the antioxidant properties of the composition. Suitable supplemental antioxidants include vitamin A, vitamin C, vitamin E, bilberry extract, carotenoids and lemon bioflavinoids. Examples of suitable carotenoids include alpha carotene, gamma carotene, lycopene, zeaxanthin, capsanthin, and lutein. In still further embodiments, the saw palmetto berry residue can be added as an adjuvant or supplement to conventional stabilizing or antioxidant agents to enhance the performance of the agents. In one embodiment, the antioxidant agent is combined with Vitamin C (ascorbic acid) or a food or vitamin supplement containing Vitamin C where the antioxidant is included in an amount effective to stabilize the Vitamin C.

In one embodiment of the invention, the saw palmetto residue is used as a dietary supplement to deliver an effective amount or dosage of an antioxidant to a mammal. The dietary supplement of the invention is primarily intended for human consumption to supply a dietary amount of an antioxidant. Preferably, the saw palmetto residue is administered orally in a suitable form that can be ingested by the subject. For example, the saw palmetto berry residue can be administered in a dietary supplement in the form of soft or hard capsules, tablets, elixirs, powders, granules, suspensions in water or non-aqueous media and as additives to a food or beverage. In preferred embodiments, the saw palmetto residue is administered in the form of capsules or tablets which can be taken daily or as needed.

The capsules or tablets, in preferred embodiments, include the saw palmetto residue as the sole or primary antioxidant composition for human consumption. The capsules or tablets preferably include a suitable vehicle or binder to retain the desired shape and size of the tablets or capsules. Suitable vehicles and binders include corn starch, lactose, sucrose, sorbitol, talc, stearic acid, magnesium stearate, dicalcium phosphate or gums. Other carriers and binders can be used as known by those skilled in the art. The vehicles and binders are preferably neutral additives that facilitate the consumption and absorption of the composition. The orally administered composition can also contain other dietary supplement components such as vitamins, minerals and nutrients.

The tablets or capsules are prepared by conventional processes. Typically, the saw palmetto residue is combined with the vehicle and binder and mixed to form a homogeneous mixture. The mixture is then formed into tablets or capsules to provide an effective unit dosage. The unit dosage is determined by conventional practices to provide a sufficient amount of the antioxidant to the animal. In one embodiment, the tablets or capsules contain about 5 to 15 grams of the saw palmetto berry residue. The dietary supplement contains at least 1 wt %, typically at least 5 wt %, and preferably at least 25 wt % of the saw palmetto residue as the primary or exclusive antioxidant. In some embodiments, the dietary supplement contains at least about 50 wt % of the saw palmetto residue and the balance other nutrients or vitamins. In another embodiment, the dietary supplement consists essentially of the saw palmetto residue.

The saw palmetto residue of the invention can also be administered as a liquid preparation for oral administration. The liquid preparations can be solutions, syrups or suspensions. The liquid preparation can also be presented in the form of a dry powder that is reconstituted with water or other suitable vehicles before use. The liquid preparations can be prepared by conventional methods with pharmaceutically acceptable additives. Additives can include suspending agents, such as sorbitol syrup, methyl cellulose, or edible fats or oils. The liquid preparation can also include emulsifying agents such as lecithin, coloring agents and sweeteners. Non-aqueous vehicles include edible plant oils, fatty acids, glycerides and fatty acid esters.

The saw palmetto residue in another embodiment is applied topically to the skin of an animal in a topical composition. The topical compositions can be in various forms commonly used for topical administration of active compounds. For example, the topical composition can be in the form of solutions, lotions, salves, creams, ointments, liposomes, sprays and gels. The topical compositions include a suitable vehicle in combination with various suspending agents, emulsifiers, coloring agents and fragrances. Examples of suitable vehicles and emulsifying agents include lecithin, isopropyl palmatate, glycerol, castor oil, olive oil, mineral oils, petrolatum, and polyethylene oxide glycols. The topical composition includes the saw palmetto residue as an antioxidant source in an amount effective to provide the desired antioxidant effect to the patient by applying the topical composition directly to the skin. In one preferred embodiment, the saw palmetto residue is obtained from an oil extraction process from dried saw palmetto berries. Preferably, the source of the antioxidant in the topical composition consists essentially of the saw palmetto residue. Preferably, the topical compositions contain at least about 1 wt % and more preferably about 1% to about 25% by weight of the saw palmetto residue. The typical composition is applied directly to the skin to deliver the saw palmetto berry residue directly to the skin. In other embodiments, the saw palmetto berry residue is added to a cosmetic composition to stabilize the oils or other components in the cosmetic composition.

While various examples have been chosen to illustrate the invention, it will be appreciated by those skilled in the art that various changes and modifications can be made without departing from the scope of the invention as defined in the appended claims.

What is claimed is:

1. A composition for administering to a patient, wherein said composition is in the form of:
   a topical composition adapted for topical application to the skin of a patient or a consumable composition adapted for oral consumption by the patient; and wherein said composition comprises:
   an antioxidant agent consisting essentially of an oil insoluble fraction obtained from saw palmetto berries, where said oil insoluble fraction is obtained by extracting saw palmetto berries with an alcohol to obtain a saw palmetto oil and alcohol extract mixture, evaporating the alcohol from the mixture to precipitate the oil insoluble fraction from the saw palmetto oil, and separating the precipitated oil insoluble fraction from the saw palmetto oil to obtain said antioxidant agent;
   said antioxidant agent being present in said composition in an amount effective to provide an effective antioxidant dosage of said antioxidant to said patient.

2. The composition of claim 1, wherein
   said antioxidant agent is substantially lipid free and free of pomace.

3. The composition of claim 1, wherein
   said antioxidant agent is included in said composition in an amount of at least 1 wt % based on the weight of the composition.

4. The composition of claim 1, wherein
   said antioxidant agent is included in said composition in an amount of at least 5.0 wt % based on the weight of the composition.

5. The composition of claim 1, wherein
   said antioxidant a ent is included in said composition in an amount of 0.1 wt % to 5 wt % based on the weight of the composition.

6. The composition of claim 1, wherein
   said antioxidant agent is included in said composition in an amount of 1 wt % to 25 wt % based on the weight of the composition.

7. The composition of claim 1, wherein
   said consumable composition is selected from the group consisting of a dietary supplement, food product and beverage.

8. The composition of claim 1, wherein
   said topical composition is selected from the group consisting of solutions, lotions, salves, creams, ointments, liposomes and gels.

9. The composition of claim 1, wherein
   said composition is a dietary supplement containing at least 50 wt % of said antioxidant agent.

10. A stabilizing composition comprising a carrier and an antioxidant agent in an amount effective to stabilize a food or dietary supplement substance, said antioxidant agent consisting essentially of an oil insoluble fraction precipitated from saw palmetto oil, where said antioxidant agent is produced by extracting saw palmetto berries with an alcohol to obtain a saw palmetto oil and alcohol extract, concentrating the saw palmetto oil and alcohol extract to remove the alcohol to form a precipitate of the oil insoluble fraction, and separating the precipitated oil insoluble fraction from the oil to obtain said antioxidant agent, and where said antioxidant agent is substantially lipid free and exhibits antioxidant properties to inhibit oxidative degradation of the substance and is substantially free of pomace.

11. The stabilizing composition of claim 10, wherein said composition contains at least 1 wt % of said antioxidant agent.

12. The stabilizing composition of claim 10, wherein said composition contains about 5 wt % or less of said antioxidant agent.

13. The stabilizing composition of claim 10, wherein said oil insoluble fraction of saw palmetto berries is deodorized.

14. A process for producing an antioxidant stabilizing composition containing an antioxidant agent comprising the step of:
   extracting saw palmetto berries with an alcohol to obtain a liquid extract containing a mixture of saw palmetto oil and alcohol;
   removing the alcohol from the mixture to precipitate an oil insoluble fraction from the saw palmetto oil; and
   removing the oil insoluble fraction from the saw palmetto oil to obtain the antioxidant agent consisting essentially of the oil insoluble fraction, where said antioxidant agent inhibits oxidative degradation of substances in contact with the antioxidant agent.

15. The process of claim 14, further comprising
   admixing said antioxidant stabilizing composition with a topical composition adapted for applying topically to a patient or a consumable composition adapted for consumption by a patient.

16. An antioxidant agent consisting essentially of the antioxidant composition obtained by the process of claim 14.

17. A topical or dietary composition comprising the antioxidant composition obtained by the process of claim 14.

* * * * *